(12) United States Patent
Fujimoto et al.

(10) Patent No.: US 6,814,848 B2
(45) Date of Patent: Nov. 9, 2004

(54) METHOD FOR DETERMINING ALLOY PHASE IN PLATING LAYER AND METHOD FOR EVALUATING SLIDING PROPERTY OF ALLOY GALVANIZED STEEL PLATE

(75) Inventors: Kyoko Fujimoto, Chiba (JP); Makoto Shimura, Chiba (JP); Yoichi Tobiyama, Chiba (JP); Kazuaki Kyono, Kurashiki (JP)

(73) Assignee: JFE Steel Corporation, Tokyo (JP)

( * ) Notice: Subject to any disclaimer, the term of this patent is extended or adjusted under 35 U.S.C. 154(b) by 32 days.

(21) Appl. No.: 10/182,780

(22) PCT Filed: Dec. 5, 2001

(86) PCT No.: PCT/JP01/10614

§ 371 (c)(1),
(2), (4) Date: Aug. 1, 2002

(87) PCT Pub. No.: WO02/46735

PCT Pub. Date: Jun. 13, 2002

(65) Prior Publication Data

US 2004/0084314 A1 May 6, 2004

(30) Foreign Application Priority Data

| Dec. 5, 2000 | (JP) | ........................................ 2000-370672 |
| Jun. 5, 2001 | (JP) | ........................................ 2001-169393 |
| Sep. 14, 2001 | (JP) | ........................................ 2001-279774 |

(51) Int. Cl.[7] .............................. C25D 21/12; C25D 5/00
(52) U.S. Cl. ............................ 205/81; 205/82; 205/84; 205/170; 205/176; 205/177
(58) Field of Search .............................. 205/81, 82, 84, 205/170, 176, 177

(56) References Cited

U.S. PATENT DOCUMENTS 5,698,085 A  * 12/1997  Yu .............................. 204/434

FOREIGN PATENT DOCUMENTS

| JP | 46-13593 | 4/1971 |
| JP | 60-164243 | 8/1985 |
| JP | 6-116699 | 4/1994 |
| JP | 9-264874 | 10/1997 |

OTHER PUBLICATIONS

Y. Tsuru et al., Yokyoku Denkaiho ni yoru Dou–Aen MekkiSoseibutsu no Kettei ni kansuru Kenkyu, Hyoumen Gijutsu, 1989, vol. 40, No. 9, pp. 1026–1030, No Month.

* cited by examiner

*Primary Examiner*—Wesley A. Nicolas
(74) *Attorney, Agent, or Firm*—Young & Thompson

(57) ABSTRACT

A method for determining a quantity of each of alloy phases in the plating layer includes subjecting each alloy phase in the plating layer to constant potential electrolysis in each of a plurality of ranges of potentials obtained on the basis of the immersion potential of each alloy phase and the immersion potential of a basis metal, by using a plated metal material having different kinds of alloy phases in the plating layer as the anode, to determine the quantity of each alloy phase in the plating layer on the basis of the quantity of electricity consumed in each range of the potentials during the electrolysis.

6 Claims, 2 Drawing Sheets

METHOD FOR DETERMINING ALLOY PHASE IN PLATING LAYER AND METHOD FOR EVALUATING SLIDING PROPERTY OF ALLOY GALVANIZED STEEL PLATE

CROSS REFERENCE TO RELATED APPLICATION

This is the 35 USC 371 national stage of International Application PCT/JP01/10614 filed on Dec. 5, 2001, which designated the United States of America.

TECHNICAL FIELD

The present invention relates to a method for determining the quantity of alloy phases (which correspond to a ζ phase, a $\delta_1$ phase, and a Γ phase in alloyed hot-dip galvanized steel sheets) in plating layers of plated metal materials and a method for evaluating the sliding property thereof.

BACKGROUND ART

Among plating layers of plated metal materials, a plating layer having a single phase of a metal and another plating layer having different kinds of alloy phases are known.

Particularly, in plated products having different kinds of alloy phases, it is known that various characteristics of the products significantly depend on the compositions and the quantity of the alloy phases.

Thus, the control of the alloy phases is essential to improve the plating characteristics.

A plating layer of an alloyed hot-dip galvanized steel sheet, of which the production is large among surface-treated steel sheets, has Zn—Fe alloy phases and is typical of plating layers having different kinds of alloy phases.

In the alloyed hot-dip galvanized steel sheets described above, the alloy phases having a significant influence on the plating characteristics correspond to Zn—Fe alloy phases (a ζ phase, a δ1 phase, and a Γ phase) Particularly, the ζ phase has a significant influence on the sliding property of alloyed hot-dip galvanized steel sheets suitable for rustproof steel sheets for automotive bodies.

In order to analyze the structure of the alloy phases of plated steel sheets, among physical techniques, the observation of a cross section of a steel sheet with an optical microscope or a scanning electron microscope is performed in general (Akihiko NISHIMURA, Jun-ichi INAGAKI, and Kazuhide NAKAOKA, Tetsu-to-Hagane, 8,101 (1986)).

According to such observation, although the degree of the growth of each alloy phase can be obtained qualitatively and the average thickness of each alloy phase can also be obtained quantitatively, there is a problem in that the preparation of samples and the observation are troublesome.

Since plated products have recently been required to have higher performance, there is a problem in that a small quantity of alloy phases adversely affects the plating characteristics.

That is, in alloyed hot-dip galvanized steel sheets, although the formation of a ζ phase and a Γ phase should be suppressed, it is difficult to identify such a small quantity of these alloy phases.

On the other hand, the relationship between the diffraction intensity of each alloy phase and the plating characteristics has been studied using X-ray diffraction, and such a technique is intended to apply analysis in a production line.

For alloyed hot-dip galvanized steel sheets, the relationship between the intensity of X-ray diffraction of each alloy phase and the sliding property or the anti-powdering property during the processing of plated steel sheets has been reported (Masato YAMADA, Aki MASUKO, Hisao HAYASHI, and Naoki MATSUURA, Current Advances in Materials and Processes, 3,591 (1990)). The application of an X-ray diffraction method to an analysis in a production line has also been reported (Junji KAWABE, Tadao FUJINAGA, Hajime KIMURA, Kazuya OSHIBA, Tadahiro ABE, and Toshio TAKAHASHI, KAWASAKI STEEL GIHO, 18,129 (1986)).

However, these techniques cannot directly give the absolute quantity of each alloy phase. In order to determine the quantity of each alloy phase in these techniques, it is necessary to make calibration curves using standard samples, of which the content of each alloy phase is known, to obtain the content on the basis of the ratio of the intensity of a measuring sample to the intensity of a standard sample.

That is, in order to determine a small quantity of a ζ phase or a Γ phase in, for example, alloyed hot-dip galvanized steel sheets, it is necessary to obtain standard samples of which the content of a ζ phase or a Γ phase is known.

On the other hand, among chemical methods, constant current anodic electrolysis (electrolytic stripping) is used. In this method, a time of a plateau of a potential corresponding to each alloy phase is obtained using a time-potential curve to determine the thickness of each alloy phase according to the quantity of electricity (S. C. Britton, J. Inst. Metals, 58,211 (1936)).

In the above method, since inflection points of the potential are not clear in alloyed hot-dip galvanized steel sheets having a small quantity of a ζ phase and a Γ phase, it is difficult to determine a small quantity of phases such as a ζ phase and a Γ phase.

Furthermore, in this method, it is difficult to dissolve each alloy phase in a plating layer uniformly.

It is reported that the direct conversion of a time of a potential plateau into the thickness of a plating layer is not correct due to the residual Γ phase having a high content of iron when applying the above method to the analysis of alloyed hot-dip galvanized steel sheets, (Susumu KUROSAWA, the Journal of the Surface Finishing Society of Japan, 45,234 (1994)).

Since the shape of the time-current curve changes depending on the surface state of a sample, it is further difficult to determine a small quantity of an alloy phase, for example, a ζ phase, situated near the surface of a plating layer in a alloyed hot-dip galvanized steel sheet.

DISCLOSURE OF INVENTION

In order to solve the above problems of conventional techniques, it is an object of the present invention to provide a method for directly determining the quantity of alloy phases (which corresponds to a ζ phase, a δ1 phase, and a Γ phase in alloyed hot-dip galvanized steel sheets) in a plating layer with preciseness and a method for evaluating the sliding property of an alloyed hot-dip galvanized steel sheet.

A first aspect of the present invention provides a method for determining a quantity of each of alloy phases in a plating layer, wherein the method includes subjecting each alloy phase in a plating layer to constant potential electrolysis in each of a plurality of ranges of potentials obtained on the basis of the immersion potential of each alloy phase and the immersion potential of a basis metal, by using a plated metal material having different kinds of alloy phases in the plating layer as the anode, to determine the quantity of each alloy phase in the plating layer on the basis of the quantity of electricity consumed in each range of the potentials during the electrolysis.

A second aspect of the present invention provides a method for determining a quantity of a ζ phase in a plating layer of an alloyed hot-dip galvanized steel sheet, wherein the method includes performing constant potential electrolysis within the range of a potential of −940 to −920 mV vs. SCE in aqueous zinc sulfate-sodium chloride using an alloyed hot-dip galvanized steel sheet as the anode to determine the quantity of a ζ phase in a plating layer on the basis of the quantity of consumed electricity.

A third aspect of the present invention provides a method for determining each quantity of a ζ phase and a $\delta_1$ phase in a plating layer of an alloyed hot-dip galvanized steel sheet, wherein the method includes performing constant potential electrolysis within the range of a potential of −940 to −920 mV vs. SCE in aqueous zinc sulfate-sodium chloride using an alloyed hot-dip galvanized steel sheet as the anode to obtain the quantity of a ζ phase in a plating layer on the basis of the quantity of consumed electricity, and then subjecting the alloyed hot-dip galvanized steel sheet, which is the anode, to constant potential electrolysis within the range of a potential of −900 to −840 mV to obtain the quantity of a $\delta_1$ phase in the plating layer on the basis of the quantity of consumed electricity.

A fourth aspect of the present invention provides a method for determining each quantity of a ζ phase, a $\delta_1$ phase, and a Γ phase in a plating layer of an alloyed hot-dip galvanized steel sheet, wherein the method includes performing constant potential electrolysis within the range of a potential of −940 to −920 mV vs. SCE in aqueous zinc sulfate-sodium chloride using an alloyed hot-dip galvanized steel sheet as the anode to obtain the quantity of a ζ phase in a plating layer on the basis of the quantity of consumed electricity, subjecting the alloyed hot-dip galvanized steel sheet, which is the anode, to constant potential electrolysis within the range of a potential of −900 to −840 mV to obtain the quantity of a $\delta_1$ phase in the plating layer on the basis of the quantity of consumed electricity, then subjecting the alloyed hot-dip galvanized steel sheet, which is the anode, to constant potential electrolysis within the range of a potential of −830 to −800 mV to obtain the quantity of a Γ phase in the plating layer on the basis of the quantity of consumed electricity.

A fifth aspect of the present invention provides a method for evaluating the sliding property of an alloyed hot-dip galvanized steel sheet, wherein the method includes performing constant potential electrolysis within the range of a potential of −940 to −920 mV vs. SCE in aqueous zinc sulfate-sodium chloride using an alloyed hot-dip galvanized steel sheet as the anode to determine the alloyed hot-dip galvanized steel sheet has a satisfactory sliding property if the quantity of consumed electricity is small.

In the fifth aspect, the quantity of consumed electricity is preferably 0.5 C/cm² or less, and the electrolysis is preferably determined to be terminated when the current density reaches 5 μm/cm².

The term "vs. SCE" used herein as the unit of potential represents a potential based on the saturated calomel electrode.

REFERENCE NUMERALS

Figure 1:
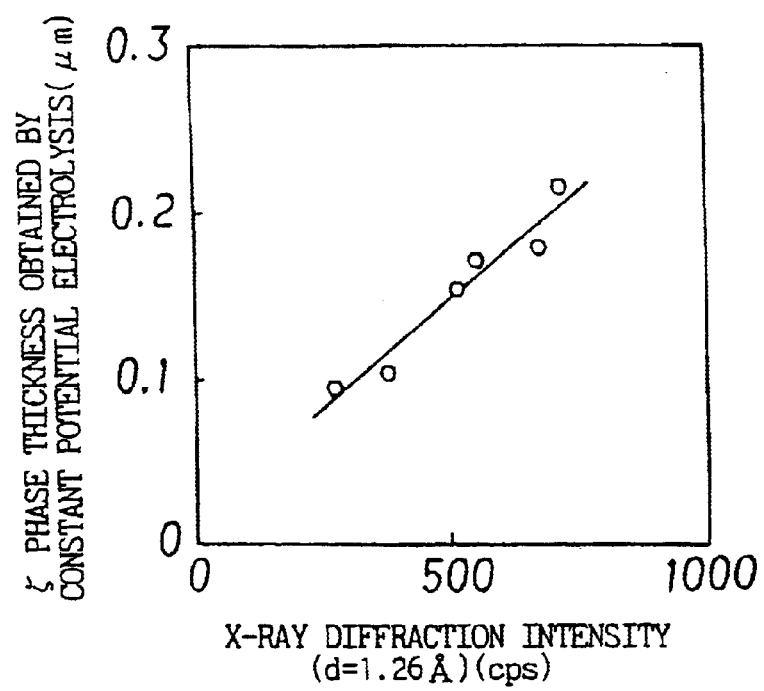
FIG. 1 is a graph (calibration curve) showing the relationship between the intensity of X-ray diffraction (d=1.26 Å) and the measured value of a ζ phase (thickness of a ζ phase) obtained by a method of the present invention.

1: electrolytic apparatus
2: sample
3: platinum ring (counter electrode)
4: saturated calomel electrode
5: platinum wire
6: electrolyte
7: reference electrode

BEST MODE FOR CARRYING OUT THE INVENTION

The present invention will now be described in detail.

The inventors have performed intensive research in order to solve the above problems. As a result, the inventors have found that each alloy phase can be determined on the basis of a quantity of electricity consumed during electrolysis which is performed with-a potential with which each alloy phase is selectively dissolved benefiting-from a structure in which each alloy phase in a plating layer is separately situated in the thickness direction of the plating layer of a plated metal material having different kinds of alloy phases.

That is, the inventors have found that the quantity of each alloy phase can be determined with high precision according to the following procedure: performing constant potential electrolysis in turn at a potential at which each of the alloy phases, which are a ζ phase, a $\delta_1$ phase, and a Γ phase, is selectively dissolved, dissolving each alloy phase, and measuring the quantity of consumed electricity at each potential, when using, for example, an alloyed hot-dip galvanized steel sheet. Actually, when an alloy phase is subjected to constant potential electrolysis selectively, there is a certain range of applicable electrolytic potential. Thus, in actual constant potential electrolysis, there is a certain range of electrolytic potential corresponding to an alloy phase.

The inventors have investigated the behavior of a ζ phase in electrolysis for alloyed hot-dip galvanized steel sheets having various sliding properties. As a result, the inventors have found that an alloyed hot-dip galvanized steel sheet has a satisfactory sliding property when a total quantity (current density×time) of electricity consumed during the electrolysis of the steel sheet is a certain value or less.

That is, a first aspect of the present invention provides a method for determining a quantity of each of alloy phases in a plating layer, wherein the method includes subjecting each alloy phase in a plating layer to constant potential electrolysis in each of a plurality of ranges of potentials obtained on the basis of the immersion potential of each alloy phase and the immersion potential of a basis metal, by using a plated metal material having different kinds of alloy phases in the plating layer as the anode, to determine the quantity of each alloy phase in the plating layer on the basis of the quantity of electricity consumed in each range of the potentials during the electrolysis.

The immersion potential described above means the potential of a metal to a saturated calomel electrode when the metal is immersed in an electrolyte. The plurality of ranges of potentials described above include potentials between the immersion potential of a basis metal and that of an alloy phase and other potentials between the immersion potentials of alloy phases.

In the above first aspect, it is preferable that each of the different kinds of alloy phases is separately situated in the thickness direction of the plating layer and the alloy phases are not mixed in the plating layer.

The reason is as follows: in the above configuration composed of different kinds of alloy phases, each alloy phase can be subjected to constant potential electrolysis from the surface of the plating layer towards the basis metal at a potential (herein referred to as a dissolution potential) at which each alloy phase is selectively dissolved to determine the quantity of each alloy phase.

The plurality of ranges of potentials described above include potentials between the immersion potential of a basis metal and that of an alloy phase (the alloy phase disposed on and directly contacting the basis metal) on the basis metal and other potentials between the immersion potentials of alloy phases contacting one another directly.

The inventors have further obtained the following finding based on the first aspect of the invention. That is, the inventors have developed a method for determining the quantity of each of a $\zeta$ phase, a $\delta_1$ phase, and a $\Gamma$ phase in a plating layer of an alloyed hot-dip galvanized steel sheet, wherein the method includes subjecting a $\zeta$ phase, a $\delta_1$ phase, and a $\Gamma$ phase, which are alloy phases in a plating layer, to constant potential electrolysis within ranges of (A) a potential of −940 to −920 mV vs. SCE, (B) a potential of −900 to −840 mV, and (C) a potential of −830 to −800 mV, respectively, in that order in aqueous zinc sulfate-sodium chloride using an alloyed hot-dip galvanized steel sheet as the anode to determine the quantity of each of the $\zeta$ phase, the $\delta_1$ phase, and the $\Gamma$ phase on the basis of the quantity of consumed electricity within each of the ranges of the potentials (A), (B), and (C). These developments lead to second to fourth aspects of the present invention.

Because, in alloyed hot-dip galvanized steel sheets, the formation of a $\delta_1$ phase and the suppression of a $\zeta$ phase and a $\Gamma$ phase are necessary.

In the second to fourth aspects, the dissolution potential is suitably set based on the kind of an alloy phase in a plating layer to selectively dissolve a predetermined alloy phase by electrolysis using a plated metal material such as an alloyed hot-dip galvanized steel sheet as an anode.

In the above operation, the quantity of electricity is measured until positive current stops flowing within the range (within the range of the dissolution potential) of electrolytic potential applicable to the selective constant potential electrolysis of a predetermined alloy phase.

When using, for example, an alloyed hot-dip galvanized steel sheet, (A) a $\zeta$ phase is subjected to electrolysis within the range of a potential of −940 to −920 mV vs. SCE until positive current stops flowing, (B) a $\delta_1$ phase is subjected to electrolysis within the range of a potential of −900 to −840 mV vs. SCE until positive current stops flowing, and (C) a $\Gamma$ phase is then subjected to electrolysis within the range of a potential of −830 to −800 mV vs. SCE until positive current stops flowing, in aqueous zinc sulfate-sodium chloride using the galvanized steel sheet as the anode.

When a potential is out of each of the above ranges, a predetermined alloy phase is not sufficiently dissolved or the selective dissolution of each alloy phase becomes difficult.

Next, the quantity of each of the $\zeta$ phase, the $\delta_1$ phase, and the $\Gamma$ phase is calculated on the basis of the electrochemical equivalent of each alloy phase and the quantity of consumed electricity within each range (within the range of electrolytic potential applicable to the selective constant potential electrolysis of a predetermined alloy phase) of potential.

The quantity of each alloy phase per unit area of the galvanized steel sheet is determined on the basis of the obtained calculation and the surface area of the galvanized steel sheet, or the thickness of each alloy phase is determined on the basis of the obtained calculation and the surface area and the density of the galvanized steel sheet.

In an alloyed hot-dip galvanized steel sheet, the quantity of each of a $\zeta$ phase, a $\delta_1$ phase, and a $\Gamma$ phase is calculated using formulas (1) and (2) below to obtain the quantity $X_i$ per unit area and the thickness of an alloy phase (alloy) i (i represents a $\zeta$ phase, a $\sigma_1$ phase, or a $\Gamma$ phase):

$$X_i(g/m^2)=[C/F]\times[M/2]\times[10000/A] \qquad (1)$$

$$Y_i(\mu m)=[C/F]\times[M/2]\times[10000/(\rho\times A)]\times10^{-6} \qquad (2)$$

wherein C represents the quantity of electricity consumed during the dissolution of an alloy phase i, F represents the Faraday constant of 96485 (C/mol), M/2 represents the average electrochemical equivalent (g/mol) of an alloy i, A represents the area (cm$^2$) of a sample subjected to the dissolution, and p represents the density (g/m$^3$) of an alloy i.

Electrolysis may be performed in a suitably selected electrolyte, and aqueous zinc sulfate-sodium chloride is preferably used when using an alloyed hot-dip galvanized steel sheet.

The reason is as follows: when using aqueous zinc sulfate-sodium chloride, the differences between the immersion potentials of a $\zeta$ phase, a $\delta_1$ phase, or a $\Gamma$ phase are large, and therefore, each alloy phase is selectively dissolved readily. Aqueous zinc sulfate-sodium chloride has advantages in that there is little chemical dissolving action on a plating layer and also there is little influence from an oxide film formed on a plating layer during electrolysis. In order to optimize the above effects, the content of zinc sulfate is preferably 1–50 mass % and the content of sodium chloride is preferably 1–30 mass %.

According to the present invention, the quantity of an alloy phase is determined directly and precisely based on the quantity of electricity consumed during electrolysis and the electrochemical equivalent of each alloy phase.

Furthermore, according to the present invention, since the quantity of each alloy phase is determined directly and precisely, the following procedure is possible: the quantity of an alloy phase of a standard sample is determined by the method of the present invention, a calibration curve is prepared based on the determined quantity and the intensity of X-ray diffraction, and the determination of the quantity of an alloy phase in a production line is then performed using the resulting calibration curve and an X-ray diffraction apparatus.

The fifth aspect of the present invention provides a method for evaluating the sliding property of an alloyed hot-dip galvanized steel sheet, wherein the method includes performing constant potential electrolysis within the range of a potential of −940 to −920 mV vs. SCE in aqueous zinc sulfate-sodium chloride using an alloyed hot-dip galvanized steel sheet as the anode to determine if the alloyed hot-dip galvanized steel sheet has a satisfactory sliding property if the quantity of consumed electricity is small.

When the quantity of electricity consumed during the constant potential electrolysis of a material is a certain value or less, the material exhibits satisfactory values in some tests for evaluating the sliding property. An exemplary test for evaluating the sliding property is a cylindrical flat-bottom cup drawing test. The constant potential electrolysis is performed within the range of a potential of −940 to −920 mV vs. SCE in aqueous zinc sulfate-sodium chloride using a plated steel sheet (alloyed hot-dip galvanized steel sheet) as the anode. The reason for the potential of −940 to −920 mV is to selectively subject a portion of an alloyed hot-dip galvanizing layer which has an influence on the sliding property to determine the quantity. The reason for the electrolysis in aqueous zinc sulfate-sodium chloride is that the solution has little chemical dissolving action on a plating layer and is hardly influenced by an oxide film formed on the surface. Since the potential used in the selective electrolysis of a portion of an alloyed hot-dip galvanizing layer which has an influence on the sliding property changes depending on changes in electrolytes, it is necessary to perform preliminary experiments to confirm the potential before changing a electrolyte.

A sixth aspect of the present invention which is a first preferred embodiment of the fifth aspect provides a method for evaluating the sliding property of an alloyed hot-dip galvanized steel sheet, wherein the quantity of electricity is 0.5 C/cm$^2$ or less in the method of the fifth aspect. The determination that the sliding property is satisfactory based on a quantity of electricity of 0.5 C/cm$^2$ or less is the same as the evaluation that the steel sheet has a satisfactory sliding property as a result of a test for evaluating the sliding property in cylindrical flat-bottom cup drawing tests. When selecting an alloyed hot-dip galvanized steel sheet having a satisfactory sliding property, it is desirable to determine on the basis of a quantity of electricity of 0.5 C/cm$^2$ or less.

A second preferred embodiment of the fifth aspect or another preferred embodiment of the sixth aspect of the present invention provides a method for evaluating the sliding property of an alloyed hot-dip galvanized steel sheet, wherein the electrolysis is determined to be terminated when the current density reaches 5 $\mu$A/cm$^2$. When the electrolysis is continued until the current density reaches 5 $\mu$A/cm$^2$, the quantity of electricity measured during the electrolysis is substantially applicable to the evaluation of the sliding property. In contrast, when the electrolysis is continued after the current density exceeds 5 $\mu$A/cm$^2$, the following disadvantages arise: increases in the cost and in the fear of incorrect results in the measurement of the quantity of electricity because the quantity of electricity according to unintended electrolysis may be measured.

EXAMPLE

The present invention will now be further illustrated with examples.

Example 1

In this example, the quantity of each of alloy phases (a $\zeta$ phase, a $\delta_1$ phase, and a $\Gamma$ phase) of an alloyed hot-dip galvanized steel sheet were determined by constant potential electrolysis.

Circular alloyed hot-dip galvanized steel sheets having a diameter of 15 mm were used as samples and a single side of each of the samples was covered with a corrosion-testing tape when the steel sheets were provided to the measurement.

The samples were three types of alloyed hot-dip galvanized steel sheets (Sample A, Sample B, and Sample C) made under different conditions. The thickness of each of the $\zeta$ phase, the $\delta 1$ phase, and the $\Gamma$ phase was measured for each sample three times.

Figure 3:
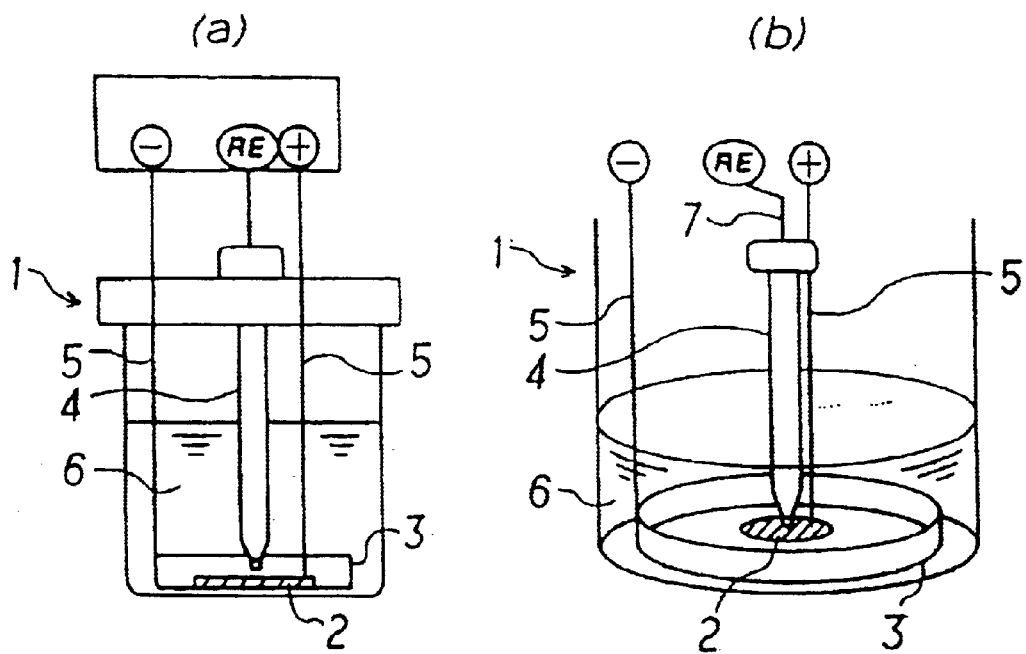
FIG. 3 includes a vertical sectional view (a) and a schematic view (b) of an electrolytic apparatus used in the examples.

FIG. 3 shows an electrolytic apparatus used for the measurement. FIG. 3(a) is a vertical sectional view thereof and FIG. 3(b) is a schematic view thereof.

In FIG. 3, reference numeral 1 denotes the electrolytic apparatus, reference-numeral 2 denotes a sample, reference numeral 3 denotes a platinum ring (counter electrode), reference numeral 4 denotes a saturated calomel electrode, reference numeral 5 denotes a platinum wire, reference numeral 6 denotes electrolyte, and reference numeral 7 denotes a reference electrode (RE).

For the electrolyte, 50 ml of an aqueous solution containing 10% of $ZnSO_4$ and 20% of NaCl was used.

As shown in FIG. 3, the saturated calomel electrode was used as a reference electrode and platinum was used for the counter electrode.

The dissolution of a $\zeta$ phase was performed at a potential of −930 mV vs. SCE, the dissolution of the $\delta_1$ phase was performed at a potential of −860 mV vs. SCE, and the dissolution of the $\Gamma$ phase was performed at a potential of −825 mV vs. SCE, in that order. For each sample, the quantity of electricity was measured until positive current stopped flowing at each potential.

Figure 4:
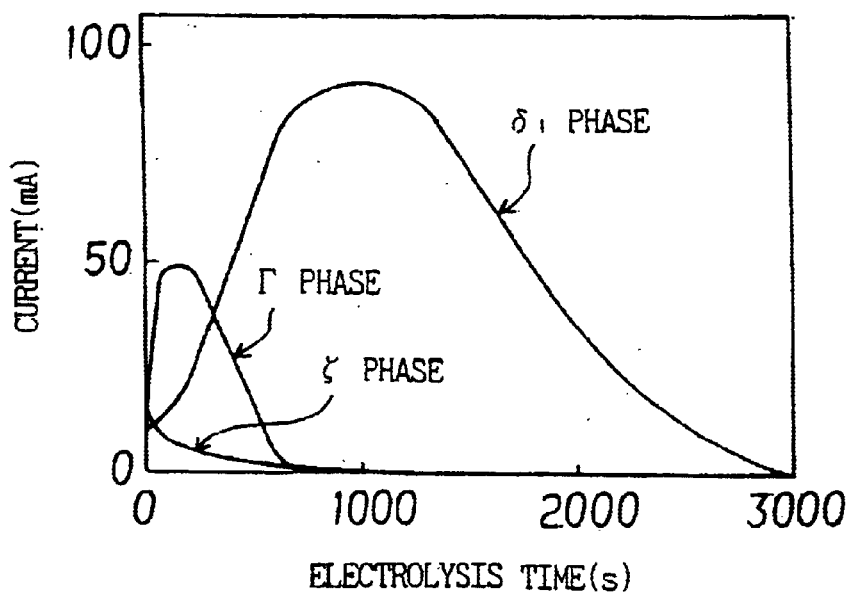
FIG. 4 is a graph showing an exemplary time-current curve of the constant potential electrolysis of a plating layer in an alloyed galvanized steel sheet.

FIG. 4 shows the time-current curve obtained in the above measurement.

Table 1 shows the thickness of each alloy phase and the standard deviation $\sigma$ of the samples made of a single plated steel sheet, wherein the thickness is calculated based on the quantity of electricity consumed during the dissolution of each alloy phase and the electrochemical equivalent of each alloy phase using the above formula (2).

In the above formula (2), the values for the symbols M/2, A, and $\rho$ are as follows: the $\zeta$ phase has a M/2 of 32.2 g/mol, the $\delta_1$ phase has a M/2 of 32.2 g/mol, the $\Gamma$ phase has a M/2 of 31.9 g/mol, the A is 1.77 cm$^2$, a $\zeta$ phase has a $\rho$ of 7.18×10$^6$ g/m$^3$, the $\delta 1$ phase has a $\rho$ of 7.25×10$^6$ g/m$^3$, and the $\Gamma$ phase has a $\rho$ of 7.36×10$^6$ g/m$^3$.

As shown in Table 1, according to the present invention, the standard deviation $\sigma$ of the measured values for samples made of a single plated steel sheet is extremely small even if there is a small quantity of each alloy phase in the plating layer. Therefore, according to the present invention, the quantity of each alloy phase can be determined directly and precisely.

Example 2

Samples used were six types of alloyed hot-dip galvanized steel sheets, which were made under different conditions. The quantity of each of a $\zeta$ phase and a $\Gamma$ phase, which were alloy phases in the alloyed hot-dip galvanized steel sheet, was determined to calculate the thickness of each alloy phase in the same way as in Example 1 according to the present invention.

Other six alloyed hot-dip galvanized steel sheets, each of which belonged to the lot of each of the above samples, were provided to measure X-ray diffraction intensity (d=1.26 Å for a $\zeta$ phase and d=2.59 Å for a $\Gamma$ phase) for the alloy phases, which are a $\zeta$ phase and a $\Gamma$ phase.

A calibration curve was then prepared based on the X-ray diffraction intensity and the measured value (the thickness of the alloy phase) was obtained by the above-described method according to the present invention.

Figure 2:
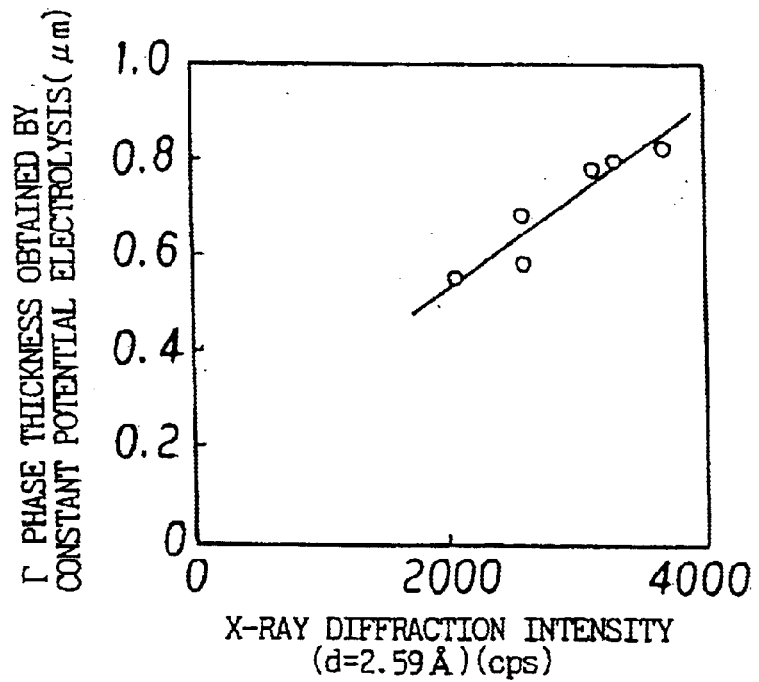
FIG. 2 is a graph (calibration curve) showing the relationship between the intensity of X-ray diffraction (d=2.59 Å) and the measured value of a Γ phase-(thickness of a Γ phase) obtained by a method of the present invention.

FIGS. 1 and 2 show the calibration curves obtained by the above method.

As shown in FIGS. 1 and 2, there is a strong relationship between the X-ray diffraction intensity and the measured value (the thickness of the alloy phase) obtained by the method according to the present invention.

From the above results, the precise determination of the quantity of an alloy phase in a production line can be performed using an X-ray diffraction apparatus and the calibration curve obtained by the method according to the present invention.

Example 3

Alloyed hot-dip galvanized steel sheets for sample materials were prepared by the procedure below.

Each of ultra low carbon steels for sample materials was melted in a converter and was then formed into a slab by continuous casting. The resulting slab was heated to 1150–1250° C., was treated at 920° C. in a final finishing step in a hot rolling process, and was then coiled at 550° C. The obtained hot rolled sheet coil having a thickness of 3.2 mm was subjected to acid pickling to remove scales, and was then cold-rolled into a cold rolled steel sheet having a thickness of 0.8 mm. The steel sheet was annealed into a plating black plate at a temperature of 790–830° C. in a continuous hot dip galvanizing line. The black plate having a temperature of 460–470° C. was immersed into a plating bath having a temperature of 460–470° C., and was then alloyed at 490–530° C. The quantity of plating on a single side was 40–50 g/m$^2$, and the quantity of plating on each side was the same.

An alloyed hot-dip galvanized steel sheet prepared by the above procedure was stamped into a disc having a diameter of 15 mm, and the disc was then subjected to constant potential electrolysis at a potential of −930 mV vs. SCE. An aqueous solution containing 20 mass % of $ZnSO_4$ and 10 mass % of NaCl was used for an electrolyte. The electrolysis was continued until the current density reached 5 $\mu A/cm^2$ to measure the quantity of electricity consumed from the start of the electrolysis. The time spent during the electrolysis was above 10–20 minutes.

A piece of each alloyed hot-dip galvanized steel sheet, a part of which was used for the above measurement of the quantity of electricity, was provided to evaluate the sliding property. Ordinary rust preventive oil was applied onto the alloyed hot-dip galvanized steel sheet piece at an amount of 1.5 g/m$^2$, and the resulting steel sheet piece was then subjected to a cup drawing test using a cylindrical flat-bottom cup having a diameter of 33 mm to obtain the limiting drawing ratio. A small rating of limiting drawing ratio corresponds to a good sliding property. A rating of 1 was given to a sample with a limiting drawing ratio of 2.0% or more, a rating of 2 was given to another sample with a limiting drawing ratio of 1.9–2.0%, a rating of 3 was given to another sample with a limiting drawing ratio of 1.8–1.9%, a rating of 4 was given to another sample with a limiting drawing ratio of 1.7–1.8%, and a rating of 5 was given to another sample with a limiting drawing ratio of 1.7% or less. The results are shown in Table 2.

Every galvanized steel sheet with an electrical quantity of 0.5 C/cm$^2$ or less has a rating of 3 or less, that is, such a galvanized steel sheet exhibits a satisfactory sliding property. In contrast, Sample 6 with an electrical quantity of more than 0.5 C/cm$^2$ has a rating of 5, that is, this sample exhibits an inferior sliding property. In particular, every galvanized steel sheet with an electrical quantity of 0.3 C/cm$^2$ or less has a rating of 1, that is, such a galvanized steel sheet exhibits an excellent sliding property.

As described above, according to the present invention, the sliding property of an alloyed hot-dip galvanized steel sheet can be evaluated.

TABLE 1

| | Thickness of Alloy Phase ($\mu$m) | | | | | | | | | | | | | | |
|---|---|---|---|---|---|---|---|---|---|---|---|---|---|---|---|
| | $\zeta$ Phase | | | | | $\delta_1$ Phase | | | | | $\Gamma$ Phase | | | | |
| Sample | 1 | 2 | 3 | Average | $\sigma$ | 1 | 2 | 3 | Average | $\sigma$ | 1 | 2 | 3 | Average | $\sigma$ |
| A | 0.10 | 0.09 | 0.09 | 0.09 | 0.01 | 4.8 | 4.9 | 4.9 | 4.9 | 0.09 | 0.86 | 0.84 | 0.81 | 0.84 | 0.03 |
| B | 0.12 | 0.14 | 0.15 | 0.14 | 0.02 | 4.8 | 4.7 | 4.9 | 4.8 | 0.09 | 0.80 | 0.78 | 0.76 | 0.78 | 0.02 |
| C | 0.18 | 0.20 | 0.20 | 0.19 | 0.01 | 4.7 | 4.4 | 4.4 | 4.5 | 0.21 | 0.56 | 0.53 | 0.56 | 0.55 | 0.02 |

Note:
$\sigma$ denotes the standard deviation.

TABLE 2

| Sample | Quantity of Plating | Content in Plating Layer | | Quantity of | Limiting |
|---|---|---|---|---|---|
| (Alloyed Hot-dip Galvanized Steel Sheet) | on Single side (g/m$^2$) | Zn (mass %) | Fe (mass %) | Electricity (C/cm$^2$) | Drawing Ratio |
| 1 | 40 | 90.4 | 9.6 | 0.13 | 1 |
| 2 | 47 | 88.3 | 11.6 | 0.16 | 1 |
| 3 | 40 | 88.5 | 11.5 | 0.21 | 1 |
| 4 | 45 | 89.6 | 10.4 | 0.30 | 1 |
| 5 | 43 | 90.1 | 9.9 | 0.47 | 3 |
| 6 | 42 | 90.0 | 10.0 | 0.55 | 5 |

Industrial Applicability

According to the present invention, the quantity of each of alloy phases can be determined directly and precisely, even if quantity of each alloy phase in a plating layer is small.

According to the present invention, an alloy phase can be quantitatively determined, although it could not be done conventionally and remarkable effects are expected in an improvement in the quality of products and stability of production.

According to the present invention, the sliding property of an alloyed hot-dip galvanized steel sheet can also be evaluated.

What is claimed is:

1. A method for determining a quantity of each of alloy phases in a plating layer comprising subjecting each alloy phase in a plating layer to constant potential electrolysis in each of a plurality of ranges of potentials obtained on the basis of the immersion potential of each alloy phase and the immersion potential of a basis metal, by using a plated metal material having different kinds of alloy phases in the plating layer as the anode, to determine the quantity of each alloy phase in the plating layer on the basis of the quantity of electricity consumed in each range of the potentials during the electrolysis.

2. A method for determining a quantity of a $\zeta$ phase in a plating layer of an alloyed hot-dip galvanized steel sheet comprising performing constant potential electrolysis within the range of a potential of −940 to −920 mV vs. SCE in aqueous zinc sulfate-sodium chloride using an alloyed hot-dip galvanized steel sheet as the anode to determine the quantity of a $\zeta$ phase in a plating layer on the basis of the quantity of consumed electricity.

3. A method for determining each quantity of a $\zeta$ phase and a $\delta_1$ phase in a plating layer of an alloyed hot-dip galvanized steel sheet comprising performing constant potential electrolysis within the range of a potential of −940 to −920 mV vs. SCE in aqueous zinc sulfate-sodium chloride using an alloyed hot-dip galvanized steel sheet as the anode to obtain the quantity of a $\zeta$ phase in a plating layer on the basis of the quantity of consumed electricity, and then subjecting the alloyed hot-dip galvanized steel sheet, which is the anode, to constant potential electrolysis within the range of a potential of −900 to −840 mV to obtain the quantity of a $\delta_1$ phase in the plating layer on the basis of the quantity of consumed electricity.

4. A method for determining each quantity of a $\zeta$ phase, a $\delta_1$ phase, and a $\Gamma$ phase in a plating layer of an alloyed hot-dip galvanized steel sheet comprising performing constant potential electrolysis within the range of a potential of −940 to −920 mV vs. SCE in aqueous zinc sulfate-sodium chloride using an alloyed hot-dip galvanized steel sheet as the anode to obtain the quantity of a $\zeta$ phase in a plating layer on the basis of the quantity of consumed electricity, subjecting the alloyed hot-dip galvanized steel sheet, which is the anode, to constant potential electrolysis within the range of a potential of −900 to −840 mV to obtain the quantity of a $\delta_1$ phase in the plating layer on the basis of the quantity of consumed electricity, then subjecting the alloyed hot-dip galvanized steel sheet, which is the anode, to constant potential electrolysis within the range of a potential of −830 to −800 mV to obtain the quantity of a $\Gamma$ phase in the plating layer on the basis of the quantity of consumed electricity.

5. A method for evaluating the sliding property of an alloyed hot-dip galvanized steel sheet comprising performing constant potential electrolysis within the range of a potential of −940 to −920 mV vs. SCE in aqueous zinc sulfate-sodium chloride using an alloyed hot-dip galvanized steel sheet as the anode to determine the alloyed hot-dip galvanized steel sheet has a satisfactory sliding property if the quantity of consumed electricity is 0.5 C/cm² or less.

6. The method for evaluating the sliding property of an alloyed hot-dip galvanized steel sheet according to claim 5, wherein the electrolysis is determined to be terminated when the current density reaches 5 $\mu$m/cm².

* * * * *